United States Patent
Zhen

(10) Patent No.: US 10,143,647 B2
(45) Date of Patent: Dec. 4, 2018

(54) GEL POLISH COMPOSITION FORMING A NAIL GEL FILM ON A KERATINOUS MATERIAL OF MAMMALS AND THE METHOD OF USING THEREOF

(71) Applicant: LiJuan Zhen, City of Industry, CA (US)

(72) Inventor: LiJuan Zhen, City of Industry, CA (US)

( * ) Notice: Subject to any disclaimer, the term of this patent is extended or adjusted under 35 U.S.C. 154(b) by 0 days.

(21) Appl. No.: 15/393,203

(22) Filed: Dec. 28, 2016

(65) Prior Publication Data

US 2018/0177710 A1    Jun. 28, 2018

Related U.S. Application Data

(60) Provisional application No. 62/279,639, filed on Jan. 15, 2016.

(51) Int. Cl.
| | | |
|---|---|---|
| *A61K 8/87* | (2006.01) | |
| *A61Q 3/02* | (2006.01) | |
| *A61K 8/81* | (2006.01) | |

(52) U.S. Cl.
CPC .............. *A61K 8/87* (2013.01); *A61K 8/8147* (2013.01); *A61Q 3/02* (2013.01); *A61K 2800/43* (2013.01); *A61K 2800/48* (2013.01)

(58) Field of Classification Search
CPC ........... A61K 8/87; A61K 8/8147; A61Q 3/02
See application file for complete search history.

(56) References Cited

U.S. PATENT DOCUMENTS

| | | | | |
|---|---|---|---|---|
| 5,202,114 A | * | 4/1993 | Ogusu .................... | A61K 8/26 106/499 |
| 2002/0136745 A1 | * | 9/2002 | Calello ................... | A61K 8/69 424/401 |
| 2004/0195377 A1 | * | 10/2004 | Williams ............... | A45D 34/04 239/378 |
| 2006/0083701 A1 | * | 4/2006 | Pagano ................ | A61K 8/8152 424/61 |
| 2007/0009474 A1 | * | 1/2007 | Xie ........................ | A61K 8/345 424/74 |
| 2008/0286299 A1 | * | 11/2008 | Battaglia .............. | A61K 9/0014 424/195.18 |
| 2010/0178262 A1 | * | 7/2010 | Kergosien ............. | A61K 8/361 424/61 |

* cited by examiner

*Primary Examiner* — Jianfeng Song
(74) *Attorney, Agent, or Firm* — Changi Wu; Changi Wu Law Office

(57) ABSTRACT

A gel polish composition forming a nail gel film on a keratinous material of mammals comprises a film-forming polymer selected from the group consisting of polyurethane resin, acrylic resin, and mixtures thereof and a method of forming a nail gel film on a keratinous material of mammals comprises: (i) cleansing the keratinous material; (ii) painting a gel polish composition on the keratinous material to form a first layer, wherein the gel polish composition comprises an film-forming polymer, a hydrophilic solvent, a thickening agent, water, and an optional care ingredient; (iii) drying the gel polish composition in air for about 1 minute; (iv) applying a second layer of the gel polish composition; (v) drying the gel polish composition in air for about 1 minute; (vi) optionally applying a third layer; and (vii) peeling off the nail gel film formed on the keratinous material of mammals without using a polish remover.

8 Claims, No Drawings

GEL POLISH COMPOSITION FORMING A NAIL GEL FILM ON A KERATINOUS MATERIAL OF MAMMALS AND THE METHOD OF USING THEREOF

CROSS-REFERENCE RELATED TO RELATED APPLICATIONS

This application claims the benefit and priority of U.S. Provisional Application No. 62/279,639, filed Jan. 15, 2016.

BACKGROUND

Traditional nail polishes based on oil or water diluent must wait for several minutes to hours to allow the oil or water to dry to form a coat on nails. Water base polish often needs an hour to dry. Even oil base polish has solvent to help evaporation of the oil, it still often takes almost 30 minutes to dry. During the drying time, the nail polish coat is soft and easy to get scratched, dented, or deteriorated. Therefore, it is desirable to dry the nail polish in a shorter time period to have a longer and better wear.

Some conventional nail polishes show faster drying rates. However, such polishes typically content nitrocellulose which tends to cause the polish coat on nail brittle and less elastic. And, it eventually becomes easier to chipping off after application on nails. Some water-based nail polishes use drying accelerators to raise the drying rate, which often causes instability of the polish that the pigment, water, and polymer to separate. The stability issue is that pigment is easy to separate from the oil and water base in 3-6 months, which especially in water base nail polish that water, raw material and pigment all separate. Water base polish has extremely bad pigmentation because the materials functionally limit.

Even oil base nail polish is better than water base nail polish, but it is still poor pigmentation in some colors. Materials can be easily dried out in storage. Especially, in water base nail polish, materials dry out after 2 to 3 months. Water and raw material easily gets residue and gets harden inside the container. Color of traditional oil or water based nail polish can dye on nature nail, which will be hard to be removed from the nail after the nail polish is dried. Some water base nail polish coat only can be peeled in small pieces from the nail surface, which remains a lot of small residues of the nail polish on nail and cannot be cleaned well without using polish remover such as acetone.

Also, some fast-drying nail polishes contain plasticizer to increase the flexibility and durability of the polymer film. Normally the plasticizer include camphor and/or dibutyl phthalate (DBP). However, dibutyl phthalate has been in a controversy linking to cancer in recent years.

Some fast-drying nail polishes also contain multiple types of polymers providing different functions, such as nitrocellulose for viscosity and polyethyl acrylate for enhancing adhesion. As stated before, nitrocellulose tends to cause the coating brittle and less elastic. The polyethyl acrylate is formed by reaction of acrylate or acrylic monomers, which may cause redness, swelling, and pain in the nail bed even if a trace of acrylate monomers is remained in the polymerized solution. Therefore, it is desired to solve these issues.

BRIEF SUMMARY OF THE INVENTION

The invention is directed to a gel polish composition forming a nail gel film on a keratinous material of mammals comprises a film-forming polymer, wherein the film-forming polymer further comprises polyurethane, and wherein the film-forming polymer is air dried to form a gel film on the at least one nail. The present invention also is related a method of forming a nail gel film on a keratinous material of mammals comprises (i) cleansing the keratinous material of mammals; (ii) painting a gel polish composition on the keratinous material of mammals to form a first layer, wherein the gel polish composition comprises an air-dry film-forming polymer, a hydrophilic solvent, a thickening agent, water, and an optional care ingredient; (iii) drying the gel polish composition in air for about 1 minute; (iv) applying a second layer of the gel polish composition; (v) drying the gel polish composition in air for about 1 minute; (vi) optionally applying a third layer of the gel polish composition.

DETAILED DESCRIPTION

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Other than in the embodiment or example, or where indicated otherwise, all numbers indicating ingredient quantities and/or reaction conditions are to be understood as being modified in every instance by the word "about," which means the ingredient quantities or reaction conditions are within 10 percent the indicated value.

Unless defined otherwise, all terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" may also include the plural referents unless the context clearly dictates otherwise.

It is further noted that the claims may be drafted to exclude any element that may be optional. As such, this statement is intended to serve as antecedent basis for use of such exclusive terminology as "solely", "only" and the like in connection with the recitation of claim elements, or the use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The disclosure is related a gel polish composition forming a nail gel film on a keratinous material of mammals comprises a film-forming polymer, wherein the film-forming polymer is selected from the group consisting of polyurethane resin, acrylic resin, and mixtures thereof, and wherein the film-forming polymer is air dried to form a gel film on the at least one nail. The current invention is also directed to a method of forming a nail gel film on a keratinous material of mammals comprises: (i) cleansing the keratinous material of mammals; (ii) painting a gel polish composition on the keratinous material of mammals to form a first layer, wherein the gel polish composition comprises an air-dry film-forming polymer, a hydrophilic solvent, a thickening agent, water, and an optional care ingredient; (iii) drying the gel polish composition in air for about 1 minute; (iv) applying a second layer of the gel polish composition; (v) drying the gel polish composition in air for about 1 minute; (vi) optionally applying a third layer of the gel polish composition; and a step to peel off the nail gel film formed on the keratinous material of mammals without using a polish remover such as acetone. The gel polish composition can be applied directly adhered to mammal nail or artificial nail for a first coat as a base coat on the nail. The gel polish composition can be further applied on the base coat and forms a second layer as decorative coat or even a third layer as top coat. The invention further comprises a hydrophilic solvent, a thickening agent, water, optional care ingredient, and the optional pigment. The air-dry film-forming polymer means that the film-forming polymer does not need ultraviolet source to cure the forming of the polymer coating on nail. The air-dry film-forming polymer forms a gel film under ambient temperature and can be air-dried. The disclosure is also related to methods of applying a long lasting and an easy-to-peel-off gel polish composition with supplemental care ingredient on nails. The care ingredient can be optionally added to the gel polish and provides a care of the keratinous material of mammals or artificial nails, such as nails, wherein the care ingredient can provide at least one of the functions of lasting moisture, anti-aging, anti-oxidation, conditioning, smoothing, flavor, and nourishing.

In one embodiment, the air-dry film-forming polymer is a polyurethane resin, which includes but not limited to Polyurethane-1, Polyurethane-2, Polyurethane-4, Polyurethane-5, Polyurethane-6, Polyurethane-8, and Polyurethane-11. Preferred embodiment uses Polyurethane-1. In another embodiment, the air-dry film-forming polymer is an acrylic resin. In another embodiment, the air-dry film-forming polymer is a mixture of acrylic resin and polyurethane resin. And, in at least one embodiment, the air-dry film-forming polymer can be from about 50% to about 90% by weight, relative to the total weight of the gel polish composition. The polyurethane resin can be in a dry form or in an aqueous form such as anionic aliphatic polyurethane dispersion. The acrylic resin can be in a dry form or an aqueous form such as acrylic dispersion too. When the acrylic resin and/or polyurethane resin is in the aqueous form, the water content of the gel polish composition is calculated from the water contained in the aqueous form.

In at least one embodiment, the hydrophilic solvent is chosen from isoprene glycol, butylene glycol, propylene glycol, glycerol, sorbitol, polyethylene glycols, dipropylene glycol methyl ether, dipropylene glycol monobutyl ether, and mixtures thereof. And, in at least one embodiment, the hydrophilic solvent can be from about 1% to about 15% by weight, relative to the total weight of the gel polish composition.

In at least one embodiment, the thickening agent may be chosen from silicates or silica, such as stearalkonium bentonite, stearalkonium hectorite, distearalkonium hectorite, and mixtures thereof. And, in at least one embodiment, the thickening agent can be from about 0.01% to about 5% by weight, relative to the total weight of the gel polish composition.

In at least one embodiment, water can be from about 5% to about 40% by weight, relative to the total weight of the gel polish composition. And, the optional pigment can be chosen from CI77891 (CAS NO. 13463-67-7), CI19140 (CAS NO. 1934-21-0), CI77510 (CAS NO. 14038-43-8), CI15850 (CAS NO. 5858-81-1), CI77019 (CAS NO. 12001-26-2), CI77499 (CAS NO. 12227-89-3), CI15880 (CAS NO. 6417-83-0), CI77742 (CAS NO. 10101-66-3), and CI77491 (CAS NO. 134-25-1).

The optional care ingredients are chosen from cosmetically acceptable ingredients. For instance, the optional care ingredients may be chosen from hyaluronic acid, amino acids, aminoacetic acid, vitamin A, vitamin C, vitamin D, d-alpha-tocopherol, magnesium 1-ascorbyl-2-phosphate, ferulic acid, ascorbic acid, ubiquinone, allantoin, 2,5-dioxo-4-imidazolidinyl, 2,3-dihydroxypropyl ester octadecanoic acid, superoxide dismutase, tocopheryl acetate, squalane (tetracosane), urea perhydrate, bioflavonoids, acetyl tyrosine, lecithin, polymethylsiloxane, glycerol (1,2,3-trihydroxypropane), and/or natural ingredients or extract of fruits or plants, such as kojic acid, licorice, mulberry, *camellia sinensis* extract, *euterpe oleracea* fruit extract, grape seed polyphenols, emollien, *oenothera biennis* oil, *aloe barbadensis* juice, *hippophae rhamnoides* fruit extract, *jojoba* esters, *vitis vinifera* (grape) fruit extract, *punica granatum* (pomegranate) extract, a mixture of one or more the natural ingredient, and derivatives thereof. In at least one embodiment, the optional care ingredients can be from about 0.001% to about 10% by weight, relative to the total weight of the gel polish composition.

Also disclosed is at least one embodiment of the gel polish composition that can be dried rapidly and easily be peeled off. In at least one embodiment of the method to apply the gel polish composition comprising about 65% by weight of a film-forming polymer relative to the total weight of the gel polish composition, wherein the film-forming polymer is selected from the group of polyurethane resin, acrylic resin, and mixtures thereof; about 5% by weight of a hydrophilic solvent relative to the total weight of the gel polish composition, wherein the hydrophilic solvent is selected from the group consisting of dipropylene glycol methyl ether, dipropylene glycol monobutyl ether, and mixtures thereof; about 5% by weight of propylene glycol, about 2.5% by weight of stearalkonium bentonite; about 17.5% by weight of water; about 2.5% by weight of optional care ingredient, and about 7.5% by weight of the optional pigment to form an easy peel-off gel polish on nails.

Also disclosed is at least one embodiment of the gel polish composition that can be dried rapidly and easily be peeled off. In at least one embodiment of the method to apply the gel polish composition comprising about 85% by weight of a film-forming polymer relative to the total weight of the gel polish composition, wherein the film-forming polymer is selected from the group of polyurethane resin, acrylic resin, and mixtures thereof; about 4% by weight of a hydrophilic solvent relative to the total weight of the gel polish composition, wherein the hydrophilic solvent is selected from the group consisting of dipropylene glycol methyl ether, dipropylene glycol monobutyl ether, and mixtures thereof; about 2.5% by weight of stearalkonium bentonite; about 5.5% by weight of water; about 3% by weight of optional care ingredient, and the optional pigment to form an easy peel-off gel polish on nails.

Also disclosed is at least one embodiment of the method applying a gel polish that can be dried rapidly and easily be peeled off. In at least one embodiment of the method to apply the gel polish composition comprising about 65% by weight of a film-forming polymer relative to the total weight of the gel polish composition, wherein the film-forming polymer is selected from the group of polyurethane resin, acrylic resin, and mixtures thereof; about 5% by weight of a hydrophilic solvent relative to the total weight of the gel polish composition, wherein the hydrophilic solvent is selected from the group consisting of dipropylene glycol methyl ether, dipropylene glycol monobutyl ether, and mixtures thereof; about 5% by weight of propylene glycol, about 2.5% by weight of stearalkonium bentonite; about 17.5% by weight of water; about 2.5% by weight of optional care ingredient, and about 7.5% by weight of the optional pigment, the steps comprise the first step to cleanse the nature nail by cleanser, the second step to paint a very thin first layer of the gel polish composition on the keratinous material of mammals, such as nails, and let the layer of the gel polish composition air-dry for about 1 minutes, and third step to paint a second layer of gel polish composition on the first layer of the gel polish composition and let the second layer of the gel polish composition air-dry for about 1 minute. In at least one embodiment, if extra moisture is desired, a top coat can be applied on the second layer. It is understood that the time to dry may be affected by the ambient temperature and the body temperature of the person having the nail to be applied with the gel polish composition. The higher the body temperature or ambient temperature is, the faster gel polish dries. The term "ambient temperature" as used herein refers to typical indoor ambient temperature and humidity conditions, for example about 58° F. to about 78° F. when relative humidity is about 25% to 75%.

Also disclosed is the layers of the gel polish composition applied on the nail can be peeled off without using any polish remover, such as acetone. In one example of applying the gel polish that can dry faster and be peeled off easily without polish remover, it can be lasted and kept moisture and health for many days. In one of the embodiment of the easy-to-peel-off gel polish composition, its benefit is understood and observed that it is safe for kids and pregnant women, no odor, better to be painted evenly than the regular polish, noninflammable, nonhazardous, and environmental friendly.

It is also disclosed is at least one embodiment of the method applying a gel polish composition that can be dried rapidly, lasting longer, able to be peeled off gel polish. In at least one embodiment of the method to apply the gel polish composition comprising about 85% by weight of film forming polymer selected from the group consisting of polyurethane resin, acrylic resin, and mixture of polyurethane resin and acrylic resin, about 4% by weight of hydrophilic solvent from the group consisting of dipropylene glycol methyl ether, dipropylene glycol monobutyl ether, and mixtures, about 2.5% by weight of stearalkonium bentonite, about 5.5% by weight of water, about 3% by weight of optional care ingredient, and the optional pigment to form an able-to-be-peel-off gel polish on nails comprising the first step to cleanse the nature nail by cleanser, the second step to paint a very thin first layer of the gel polish composition on the keratinous material of mammals, such as nails, and let the layer of the gel polish composition air-dry for about 1 minute, and third step to paint a second layer of the gel polish composition on the first layer of the gel polish composition and let the second layer of the gel polish composition air-dry for about 1 minute. The second layer of the gel polish is regular thin. In at least one embodiment, if extra moisture is desired, a top coat can be applied on the second layer. It is understood that the time to dry may be affected by the ambient temperature and the body temperature of the person having the nail to be applied with the gel polish composition. The higher the body temperature or ambient temperature is, the faster gel polish dries.

Also disclosed is the layers of the gel polish composition that can be lasted longer can be peeled off without using polish remover, such as acetone.

In one example of applying the gel polish that can dry faster and last longer, the time to dry can be two times faster than traditional or conventional polish, but it can be lasted and kept moisture and health effects. In one of the embodiment of the easy-to-peel-off gel polish, its benefit is understood and observed that it is moisture and shines, no odor, safe for kids and pregnant women, better pigment coverage and smoother painting, noninflammable and environmental friendly.

Having described the subject matter of the present disclosure detailed description of embodiments and examples for purposes of clarity of understanding to a person with ordinary skill in the art that the same can be performed by modifying or changing the subject matter within various conditions, by various formulations and by other parameters without affecting its scope or any specific embodiment thereof, and that such modifications or changes are intended to be encompassed within the scope of the claims.

In one of the embodiment of the gel polish composition which comprises an air-dry film-forming polymer, hydrophilic solvent, a thickening agent, water, and an optional care ingredient, wherein the gel polish composition is in a sprayable form, which can be in pressured can, aerosol can, or spraying device to spray the gel polish composition on nail.

What is claimed:

1. A gel polish composition forming a nail gel film on a keratinous material of mammals, consisting of: a film-forming polymer in an amount of from about 67.5% to about 90% by weight, relative to the total weight of the gel polish composition, wherein the film-forming polymer is selected from the group consisting of polyurethane resin, acrylic resin, and mixtures thereof; hydrophilic solvent; a thickening agent; water, and an optional care ingredient.

2. The gel polish composition of claim 1, wherein the hydrophilic solvent is present in an amount of from about 1% to about 15% by weight, relative to the total weight of the gel polish composition, and wherein the hydrophilic solvent is selected from the group consisting of isoprene glycol, butylene glycol, propylene glycol, glycerol, sorbitol, polyethylene glycols, dipropylene glycol methyl ether, dipropylene glycol monobutyl ether, a mixture of one or more the hydrophilic solvent, and derivatives thereof.

3. The gel polish composition of claim 1, wherein the thickening agent is selected from the group consisting of stearalkonium bentonite, stearalkonium hectorite, distearalkonium hectorite, and mixtures thereof, and wherein the thickening agent is present in an amount of from about 0.01% to about 5% by weight, relative to the total weight of the gel polish composition.

4. The gel polish composition of claim 1, wherein the water is present in an amount of from about 5% to about 40% by weight, relative to the total weight of the gel polish composition.

5. The gel polish composition of claim 1, wherein the optional care ingredient is cosmetically safe, wherein the optional care ingredient is selected from the group consisting of hyaluronic acid, amino acids, aminoacetic acid, vitamin A, vitamin C, vitamin D, d-alpha-tocopherol, magnesium 1-ascorbyl-2-phosphate, ferulic acid, ascorbic acid, ubiquinone, allantoin, 2,5-dioxo-4-imidazolidinyl, 2,3-dihydroxypropyl ester octadecanoic acid, superoxide dismutase, tocopheryl acetate, squalane, urea perhydrate, bioflavonoids, acetyl tyrosine, lecithin, polymethylsiloxane, glycerol, natural ingredients, extract of fruits, extract of plants, a mixture of one or more the optional care ingredient, and derivatives thereof, and wherein the optional care ingredient is present in an amount of from about 0.001% to about 10% by weight, relative to the total weight of the gel polish composition.

6. The gel polish composition of claim 5 wherein the natural ingredients are selected from the group consisting of kojic acid, licorice, mulberry, *camellia sinensis* extract, *euterpe oleracea* fruit extract, grape seed polyphenols, emollien, *aloe barbadensis* juice, *hippophae rhamnoides* fruit extract, *jojoba* esters, *vitis vinifera* fruit extract, *punica granatum* extract, a mixture of one or more the natural ingredient, and derivatives thereof.

7. The gel polish composition of claim 1, further comprising: an optional pigment, wherein the pigment is selected from the group consisting of CI77891, CI19140, CI77510, CI15850, CI77019, CI77499, CI15880, CI77742, and CI77491, and mixtures thereof.

8. The gel polish composition of claim 1, wherein the gel polish composition is in a sprayable form.

* * * * *